United States Patent
Hossainy et al.

(10) Patent No.: US 8,119,184 B2
(45) Date of Patent: Feb. 21, 2012

(54) METHOD OF MAKING A VARIABLE SURFACE AREA STENT

(75) Inventors: Syed Hossainy, Fremont, CA (US); Fuh-Wei Tang, Temecula, CA (US); Brian P. Cahill, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/688,571

(22) Filed: Jan. 15, 2010

(65) Prior Publication Data
US 2010/0116785 A1    May 13, 2010

Related U.S. Application Data

(62) Division of application No. 10/819,776, filed on Apr. 6, 2004, now Pat. No. 7,674,493, which is a division of application No. 09/834,012, filed on Apr. 12, 2001, now Pat. No. 6,764,505.

(51) Int. Cl.
*A61L 33/00* (2006.01)
*B05D 3/12* (2006.01)
*B05D 3/10* (2006.01)

(52) U.S. Cl. ....... 427/2.24; 427/2.1; 427/2.25; 427/264; 427/271; 427/307; 623/1.15; 623/1.42; 623/1.45; 623/1.46

(58) Field of Classification Search ............ 427/2.1, 427/2.24, 2.25; 623/1.1, 1.15, 1.42, 1.43, 623/1.45, 1.46
See application file for complete search history.

(56) References Cited

U.S. PATENT DOCUMENTS

| | | | |
|---|---|---|---|
| 2,072,303 | A | 3/1937 | Herrmann et al. |
| 4,733,665 | A | 3/1988 | Palmaz |
| 4,800,882 | A | 1/1989 | Gianturco |
| 4,886,062 | A | 12/1989 | Wiktor |
| 4,931,287 | A | 6/1990 | Bae et al. |
| 4,977,901 | A | 12/1990 | Ofstead |
| 4,994,560 | A | 2/1991 | Kruper, Jr. et al. |
| 5,040,548 | A | 8/1991 | Yock |
| 5,059,166 | A | 10/1991 | Fischell et al. |
| 5,064,435 | A | 11/1991 | Porter |
| 5,087,244 | A | 2/1992 | Wolinsky et al. |

(Continued)

FOREIGN PATENT DOCUMENTS

DE    19916086    10/1999

(Continued)

OTHER PUBLICATIONS

Final Office Action for U.S. Appl. No. 10/835,229, mailed Apr. 18, 2011, 14 pgs.

(Continued)

*Primary Examiner* — Timothy Meeks
*Assistant Examiner* — Cachet Sellman
(74) *Attorney, Agent, or Firm* — Squire Sanders (US) LLP

(57) ABSTRACT

A stent of variable surface area as determined by stent struts. The stent can have a variable surface area per unit length which accommodates a therapeutic agent. A patterned distribution of therapeutic agent can be provided throughout the stent. The stent can have an increased level of therapeutic agent near an end of the stent. A decreased level of therapeutic agent can be provided near an end of one embodiment of a stent. Indentations can be provided at the surface of the stent with therapeutic agent disposed therein. The stent can be cut with struts of variable thickness to provide the variable stent surface area.

17 Claims, 4 Drawing Sheets

U.S. PATENT DOCUMENTS

| | | | |
|---|---|---|---|
| 5,100,429 A | 3/1992 | Sinofsky et al. | |
| 5,213,561 A | 5/1993 | Weinstein et al. | |
| 5,229,172 A | 7/1993 | Cahalan et al. | |
| 5,232,444 A | 8/1993 | Just et al. | |
| 5,258,419 A | 11/1993 | Rolando et al. | |
| 5,278,200 A | 1/1994 | Coury et al. | |
| 5,308,641 A | 5/1994 | Cahalan et al. | |
| 5,328,471 A | 7/1994 | Slepian | |
| 5,336,518 A | 8/1994 | Narayanan et al. | |
| 5,342,283 A | 8/1994 | Good | |
| 5,342,621 A | 8/1994 | Eury | |
| 5,344,425 A | 9/1994 | Sawyer | |
| 5,344,455 A | 9/1994 | Keogh et al. | |
| 5,350,800 A | 9/1994 | Verhoeven et al. | |
| 5,366,504 A | 11/1994 | Andersen et al. | |
| 5,411,466 A | 5/1995 | Hess | |
| 5,415,938 A | 5/1995 | Cahalan et al. | |
| 5,429,618 A | 7/1995 | Keogh | |
| 5,441,515 A | 8/1995 | Khosravi et al. | |
| 5,443,496 A | 8/1995 | Schwartz et al. | |
| 5,464,450 A | 11/1995 | Buscemi et al. | |
| 5,464,650 A | 11/1995 | Berg et al. | |
| 5,470,313 A | 11/1995 | Crocker et al. | |
| 5,476,509 A | 12/1995 | Keogh et al. | |
| 5,500,013 A | 3/1996 | Buscemi et al. | |
| 5,551,954 A | 9/1996 | Buscemi et al. | |
| 5,554,182 A | 9/1996 | Dinh et al. | |
| 5,571,166 A | 11/1996 | Dinh et al. | |
| 5,578,073 A | 11/1996 | Haimovich et al. | |
| 5,591,224 A | 1/1997 | Schwartz et al. | |
| 5,591,227 A | 1/1997 | Dinh et al. | |
| 5,593,434 A | 1/1997 | Williams | |
| 5,599,352 A | 2/1997 | Dinh et al. | |
| 5,605,696 A | 2/1997 | Eury et al. | |
| 5,624,411 A | 4/1997 | Tuch | |
| 5,628,730 A | 5/1997 | Shapland et al. | |
| 5,628,785 A | 5/1997 | Schwartz et al. | |
| 5,637,113 A | 6/1997 | Tartaglia et al. | |
| 5,649,951 A | 7/1997 | Davidson | |
| 5,649,977 A | 7/1997 | Campbell | |
| 5,667,767 A | 9/1997 | Greff et al. | |
| 5,670,558 A | 9/1997 | Onishi et al. | |
| 5,674,242 A | 10/1997 | Phan et al. | |
| 5,693,085 A | 12/1997 | Buirge et al. | |
| 5,693,376 A | 12/1997 | Fetherston et al. | |
| 5,697,967 A | 12/1997 | Dinh et al. | |
| 5,700,286 A | 12/1997 | Tartaglia et al. | |
| 5,702,818 A | 12/1997 | Cahalan et al. | |
| 5,707,385 A | 1/1998 | Williams | |
| 5,711,812 A | 1/1998 | Chapek et al. | |
| 5,713,949 A | 2/1998 | Jayaraman | |
| 5,716,981 A | 2/1998 | Hunter et al. | |
| 5,722,984 A | 3/1998 | Fischell et al. | |
| 5,730,698 A | 3/1998 | Fischell et al. | |
| 5,766,710 A | 6/1998 | Turnlund et al. | |
| 5,769,883 A | 6/1998 | Buscemi et al. | |
| 5,769,884 A | 6/1998 | Solovay | |
| 5,782,742 A | 7/1998 | Crocker et al. | |
| 5,800,392 A | 9/1998 | Racchini | |
| 5,810,873 A | 9/1998 | Morales | |
| 5,811,151 A | 9/1998 | Hendriks et al. | |
| 5,824,048 A | 10/1998 | Tuch | |
| 5,824,049 A | 10/1998 | Ragheb et al. | |
| 5,826,586 A | 10/1998 | Mishra et al. | |
| 5,830,178 A | 11/1998 | Jones et al. | |
| 5,837,313 A | 11/1998 | Ding et al. | |
| 5,840,009 A | 11/1998 | Fischell et al. | |
| 5,843,172 A | 12/1998 | Yan | |
| 5,851,508 A | 12/1998 | Greff et al. | |
| 5,857,998 A | 1/1999 | Barry | |
| 5,858,556 A | 1/1999 | Eckert et al. | |
| 5,858,990 A | 1/1999 | Walsh | |
| 5,865,814 A | 2/1999 | Tuch | |
| 5,866,113 A | 2/1999 | Hendriks et al. | |
| 5,871,436 A | 2/1999 | Eury | |
| 5,871,437 A | 2/1999 | Alt | |
| 5,873,904 A | 2/1999 | Ragheb et al. | |
| 5,893,840 A | 4/1999 | Hull et al. | |
| 5,897,911 A | 4/1999 | Loeffler | |
| 5,898,178 A | 4/1999 | Bunker | |
| 5,902,631 A | 5/1999 | Wang et al. | |
| 5,916,234 A | 6/1999 | Lam | |
| 5,925,552 A | 7/1999 | Keogh et al. | |
| 5,928,916 A | 7/1999 | Keogh | |
| 5,947,993 A | 9/1999 | Morales | |
| 5,951,881 A | 9/1999 | Rogers et al. | |
| 5,968,091 A | 10/1999 | Pinchuk et al. | |
| 5,968,092 A | 10/1999 | Buscemi et al. | |
| 5,971,954 A | 10/1999 | Conway et al. | |
| 5,972,027 A * | 10/1999 | Johnson | 623/1.42 |
| 5,972,029 A | 10/1999 | Fuisz | |
| 5,980,564 A | 11/1999 | Stinson | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,013,099 A | 1/2000 | Dinh et al. | |
| 6,015,541 A | 1/2000 | Greff et al. | |
| 6,019,789 A | 2/2000 | Dinh et al. | |
| 6,024,918 A | 2/2000 | Hendriks et al. | |
| 6,027,526 A | 2/2000 | Limon et al. | |
| 6,033,719 A | 3/2000 | Keogh | |
| 6,042,606 A | 3/2000 | Frantzen | |
| 6,042,875 A | 3/2000 | Ding et al. | |
| 6,059,752 A | 5/2000 | Segal | |
| 6,071,305 A | 6/2000 | Brown et al. | |
| 6,080,099 A | 6/2000 | Slater et al. | |
| 6,080,190 A | 6/2000 | Schwartz | |
| 6,093,199 A | 7/2000 | Brown et al. | |
| 6,096,070 A | 8/2000 | Ragheb et al. | |
| 6,099,455 A | 8/2000 | Columbo et al. | |
| 6,099,559 A | 8/2000 | Nolting | |
| 6,099,561 A | 8/2000 | Alt | |
| 6,106,454 A | 8/2000 | Berg et al. | |
| 6,110,483 A | 8/2000 | Whitbourne et al. | |
| 6,140,127 A | 10/2000 | Sprague | |
| 6,140,431 A | 10/2000 | Kinker et al. | |
| 6,149,574 A | 11/2000 | Trauthen et al. | |
| 6,153,252 A | 11/2000 | Hossainy et al. | |
| 6,165,212 A | 12/2000 | Dereume et al. | |
| 6,168,619 B1 | 1/2001 | Dinh et al. | |
| 6,203,551 B1 | 3/2001 | Wu | |
| 6,214,901 B1 | 4/2001 | Chudzik et al. | |
| 6,224,894 B1 | 5/2001 | Jamiolkowski et al. | |
| 6,231,590 B1 | 5/2001 | Slaikeu et al. | |
| 6,242,041 B1 | 6/2001 | Katoot et al. | |
| 6,253,443 B1 | 7/2001 | Johnson | |
| 6,254,632 B1 | 7/2001 | Wu et al. | |
| 6,258,121 B1 | 7/2001 | Yang et al. | |
| 6,262,034 B1 | 7/2001 | Mathiowitz et al. | |
| 6,273,850 B1 | 8/2001 | Gambale et al. | |
| 6,273,913 B1 | 8/2001 | Wright et al. | |
| 6,287,628 B1 * | 9/2001 | Hossainy et al. | 427/2.3 |
| 6,296,603 B1 | 10/2001 | Turnlund et al. | |
| 6,319,520 B1 | 11/2001 | Wuthrich et al. | |
| 6,344,035 B1 | 2/2002 | Chudzik et al. | |
| 6,379,379 B1 | 4/2002 | Wang | |
| 6,379,381 B1 | 4/2002 | Hossainy et al. | |
| 6,395,326 B1 | 5/2002 | Castro et al. | |
| 6,413,272 B1 | 7/2002 | Igaki | |
| 6,481,262 B2 | 11/2002 | Ching et al. | |
| 6,488,701 B1 | 12/2002 | Nolting et al. | |
| 6,504,307 B1 | 1/2003 | Malik et al. | |
| 6,510,722 B1 | 1/2003 | Ching et al. | |
| 6,524,232 B1 | 2/2003 | Tang et al. | |
| 6,554,758 B2 | 4/2003 | Turnlund et al. | |
| 6,558,733 B1 | 5/2003 | Hossainy et al. | |
| 6,582,417 B1 | 6/2003 | Ledesma et al. | |
| 6,596,296 B1 | 7/2003 | Nelson et al. | |
| 6,605,114 B1 | 8/2003 | Yan et al. | |
| 6,652,575 B2 | 11/2003 | Wang | |
| 6,656,216 B1 | 12/2003 | Hossainy et al. | |
| 6,663,662 B2 | 12/2003 | Pacetti et al. | |
| 6,699,281 B2 | 3/2004 | Vallana et al. | |
| 6,764,505 B1 | 7/2004 | Hossainy et al. | |
| 6,783,543 B2 | 8/2004 | Jang | |
| 6,783,793 B1 | 8/2004 | Hossainy et al. | |

| | | |
|---|---|---|
| 6,805,709 B1 | 10/2004 | Schaldach et al. |
| 6,805,898 B1 | 10/2004 | Wu et al. |
| 6,849,089 B2 | 2/2005 | Stoll |
| 6,918,927 B2 | 7/2005 | Bates et al. |
| 6,939,376 B2 | 9/2005 | Shulze et al. |
| 7,077,859 B2 | 7/2006 | Sirhan et al. |
| 7,083,642 B2 | 8/2006 | Sirhan et al. |
| 7,135,038 B1 | 11/2006 | Limon |
| 7,135,039 B2 | 11/2006 | De Scheerder et al. |
| 7,169,178 B1 | 1/2007 | Santos et al. |
| 7,208,011 B2 | 4/2007 | Shanley et al. |
| 7,279,175 B2 | 10/2007 | Chen et al. |
| 7,445,629 B2 | 11/2008 | Rosenthal et al. |
| 7,585,320 B2 | 9/2009 | Hamm et al. |
| 7,607,208 B2 | 10/2009 | Curcio et al. |
| 7,632,307 B2 | 12/2009 | Pacetti et al. |
| 7,674,493 B2 | 3/2010 | Hossainy et al. |
| 7,820,229 B2 | 10/2010 | Santos et al. |
| 7,824,440 B2 | 11/2010 | Santos et al. |
| 7,824,441 B2 | 11/2010 | Santos et al. |
| 2002/0007209 A1 | 1/2002 | Scheerder et al. |
| 2002/0183581 A1 | 12/2002 | Yoe et al. |
| 2003/0033007 A1 | 2/2003 | Sirhan et al. |
| 2003/0068355 A1 | 4/2003 | Shanley et al. |
| 2003/0074049 A1 | 4/2003 | Hoganson et al. |
| 2003/0088307 A1 | 5/2003 | Shulze et al. |
| 2003/0105964 A1 | 6/2003 | Brainard et al. |
| 2003/0139801 A1 | 7/2003 | Sirhan et al. |
| 2003/0153901 A1 | 8/2003 | Herweck et al. |
| 2004/0122506 A1 | 6/2004 | Shanley et al. |
| 2004/0127976 A1 | 7/2004 | Diaz |
| 2004/0191404 A1 | 9/2004 | Hossainy et al. |
| 2004/0254638 A1 | 12/2004 | Byun et al. |
| 2005/0107864 A1 | 5/2005 | Hong et al. |
| 2005/0211680 A1 | 9/2005 | Li et al. |
| 2005/0228482 A1 | 10/2005 | Herzog et al. |
| 2006/0149365 A1 | 7/2006 | Fifer et al. |
| 2006/0200231 A1 | 9/2006 | O'Brien et al. |
| 2006/0224234 A1 | 10/2006 | Jayaraman |
| 2007/0123977 A1 | 5/2007 | Cottone et al. |
| 2007/0173923 A1 | 7/2007 | Savage et al. |
| 2007/0196433 A1 | 8/2007 | Ron et al. |
| 2007/0207186 A1 | 9/2007 | Scanlon et al. |
| 2008/0077218 A1 | 3/2008 | McMorrow et al. |
| 2008/0140186 A1 | 6/2008 | Grignani et al. |
| 2009/0005861 A1 | 1/2009 | Hossainy et al. |
| 2009/0030507 A1 | 1/2009 | Klocke et al. |
| 2009/0165295 A1 | 7/2009 | Cohen et al. |
| 2009/0208555 A1 | 8/2009 | Kuttler et al. |
| 2010/0042205 A1 | 2/2010 | Atanasoska et al. |
| 2010/0057188 A1 | 3/2010 | Weber |
| 2010/0131046 A1 | 5/2010 | Santos et al. |
| 2011/0008528 A1 | 1/2011 | Santos et al. |

FOREIGN PATENT DOCUMENTS

| | | |
|---|---|---|
| EP | 0 627 226 | 12/1994 |
| EP | 0 665 023 | 8/1995 |
| EP | 0 701 803 | 3/1996 |
| EP | 0 850 604 | 7/1998 |
| EP | 0 970 711 | 1/2000 |
| EP | 0 972 498 | 1/2000 |
| EP | 0 850 651 | 6/2000 |
| EP | 1 103 234 | 5/2001 |
| WO | WO 90/01969 | 3/1990 |
| WO | WO 91/12846 | 9/1991 |
| WO | WO 97/45105 | 12/1997 |
| WO | WO 98/23228 | 6/1998 |
| WO | WO 99/63981 | 12/1999 |
| WO | WO 00/12147 | 3/2000 |
| WO | WO 00/64506 | 11/2000 |
| WO | WO 01/01890 | 1/2001 |
| WO | WO 01/45763 | 6/2001 |
| WO | WO 01/91918 | 12/2001 |
| WO | WO 02/47731 | 6/2002 |
| WO | WO 02/083039 | 10/2002 |
| WO | WO 2004/000379 | 12/2003 |

OTHER PUBLICATIONS

Barath et al., *Low Dose of Antitumor Agents Prevents Smooth Muscle Cell Proliferation After Endothelial Injury*, JACC 13(2):252A (1989) (Abstract).

Crowe et al., *Absorption and Intestinal Metabolism of SDZ-RAD and Rapamycin in Rats*, Drug Metabolism and Disposition, vol. 27, No. 5, pp. 627-632 (1999).

*FFS700 MSI Balloon Form/Fold/Set Equipment (PTCA), FFS800 MSI Balloon Form/Fold/Set Equipment (PTA)*, Machine Solutions, http://machinesolutions.org/ffs7_8.html, 2 pages, printed Nov. 21, 2003.

Fischell et al., *Low-Dose, β-Particle Emission from 'Stant' Wire Results in Complete, Localized Inhibition of Smooth Muscle Cell Proliferation*, Circulation, vol. 90(6):2956-2963, Dec. 1994.

Fischell et al., *The Bx Velocity™ Stent* (Biocompatibles Ltd.), 5 pages (2001).

Gercken et al., *Results of the Jostent Coronary Stent Graft Implantation in Various Clinical Settings: Procedural and Follow-Up Results*, vol. 56, No. 3, pp. 353-360 (2002).

*Guidant Multi-Link Vision OTW Coronary Stent System*, 2 pages.

Hehrlein et al., "*Low-Dose Radioactive Endovascular Stents Prevent Smooth Muscle Cell Proliferation and Neointimal Hyperplasia in Rabbits*", Circulation, vol. 92(6):1570-1575, Sep. 15, 1995 (printed Dec. 4, 2003).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Lemos et al., *Coronary Restenosis After Sirolimus-Eluting Stent Implantation*, Circulation, vol. 108, No. 3, pp. 257-260 (Jul. 22, 2003).

Liermann et al., *Prophylactic Endovascular Radiotherapy to Prevent Intimal Hyperplasia after Stent Implantation in Femoropopliteal Arteries*, CardioVascular and Interventional Radiology 17:12-16, 1994.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A 15(6):2875-2879 (Nov./Dec. 1997).

Malik et al., *Overview of Plasma Source Ion Implantation Research at University of Wisconsin-Madison*, J. Vac. Sci. Technol. B 12(2):843-849 (Mar./Apr. 1994).

Malik et al., *Sheath Dynamics and Dose Analysis for Planar Targets in Plasma Source Ion Implantation*, Plasma Sources Sci. Technol. 2:81-85 (1993).

Matsumaru et al., *Embolic Materials for Endovascular Treatment of Cerebral Lesions*, J. Biomater. Sci. Polymer Edn. 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6):2490-2498 (1985).

Miyazawa et al., *Effects of Pemirolast and Tranilast on Intimal Thickening After Arterial Injury in the Rat*, J. Cardiovasc. Pharmacol. 30(2):157-162 (1997).

Ohsawa et al., *Preventive Effects of an Antiallergic Drug, Pemirolast Potassium, on Restenosis After Percutaneous Transluminal Coronary Angioplasty*, Am. Heart J. 136(6):1081-1087 (Dec. 1998).

*SC700 MSI Stent Crimping Equipment (PTCS), SC800 MSI Stent Crimping Equipment (PTA)*, Machine Solutions, http://www.machinesolutions.org/sc7_8.html, 2 pages, printed Nov. 21, 2003.

Scheuer et al., *Model of Plasma Source Ion Implantation in Planar, Cylindrical, and Spherical Geometries*, J. Appl. Phys. 67(3):1241-1245 (Feb. 1990).

Serkova et al., *Tissue Distribution and Clinical Monitoring of the Novel Macrolide Immunosuppressant SDZ-RAD and its Metabolites in Monkey Lung Transplant Recipients: Interaction with*

*Cyclosporine*, The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent*, Circulation 101:3-7 (Jan. 2000).

Shamim et al., *Measurement of Electron Emission Due to Energetic Ion Bombardment in Plasma Source Ion Implantation*, J. Appl. Phys. 70(9):4756-4759 (Nov. 1991).

Shamim et al., *Measurements of Spatial and Temporal Sheath Evolution for Spherical and Cylindrical Geometrics in Plasma Source Ion Implantation*, J. Appl. Phys. 69(5):2904-2908 (Mar. 1991).

Shigeno, *Prevention of Cerebrovascular Spasm by Bosentan, Novel Endothelin Receptor*, Chem. Abstracts 125:212307 (1996).

van der Giessen et al., *"Edge Effect" of $^{32}P$ Radioactive Stents is Caused by the Combination of Chronic Stent Injury and Radioactive Dose Falloff*, Circulation 104:2236-2241 (Oct. 30, 2001).

Wiesendanger, *Contributions of Scanning Probe Microscopy and Spectroscopy to the Investigation and Fabrication of Nanometer-Scale Structures*, J. Vac. Sci. Technol. B, 12(2):515-529 (Mar./Apr. 1994).

Zimarino et al., Analysis of Stent Edge Restenosis with Different Forms of Brachytherapy, The American Journal of Cardiology, vol. 89, pp. 322-325 (Feb. 1, 2002).

\* cited by examiner

METHOD OF MAKING A VARIABLE SURFACE AREA STENT

CROSS-REFERENCE TO RELATED APPLICATIONS

This application is a divisional of application Ser. No. 10/819,776, filed Apr. 6, 2004, now U.S. Pat. No. 7,674,493, which is a divisional of application Ser. No. 09/834,012, filed Apr. 12, 2001, now U.S. Pat. No. 6,764,505, the entire disclosure and contents of both applications are incorporated herein by reference.

BACKGROUND OF THE INVENTION

The present invention relates to intravascular implants. In particular, the present invention relates to stent devices to deliver therapeutic agents such as radioisotopes or drugs.

BACKGROUND OF THE PRIOR ART

In the last several years, minimally invasive surgical procedures have become increasingly common. Minimally invasive procedures such as percutaneous transluminal coronary angioplasty (PTCA) are widely utilized. A PTCA procedure involves the insertion of an angioplasty balloon at the distal end of a catheter to the site of a stenotic lesion. Prior to treatment, the stenotic lesion is bulky and at least partially blocking the coronary artery at issue. Once advanced, the balloon is inflated compressing the stenosis and widening the lumen in order to allow an efficient flow of blood through the lumen.

Following PTCA and other stenotic treatment procedures, a significant number of patients may experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. A stent is a tubular structure which is delivered to the site of the former stenosis or lesion and compressed against vessel walls thereat, again with a balloon. The structure of the stent promotes maintenance of an open vessel lumen. The stent can be implanted in conjunction with the angioplasty.

In addition to stent implantation, radiotherapy and drug delivery treatments have been developed and applied to the site of the former stenosis following angioplasty. Generally such treatments can aid in the healing process and significantly reduce the risk of restenosis and other similar problems.

In some cases, stent implantation may be combined with drug delivery or radiotherapy. For example, a stent may be drug loaded or radioactive. A stent with a therapeutic agent may be delivered to the physician about the stent delivery catheter (and with a removable shield if the stent is radioactive).

However, delivery of a therapeutic treatment throughout the site of the former stenosis is problematic. The level of uniformity in the delivery of a therapeutic agent to the injured area is dependent upon the particular stent configuration. For example, in the case a radioactive stent, the radioactive stent may have hot spots and cold spots of uneven levels of radioactivity. This is because the stent is made up of struts having radioactivity and window cells having no physical structure or radioactivity (or drug in the case of a drug delivery stent). Therefore, therapeutic agent throughout a particular stent configuration is dependent upon the strut and window cell distribution throughout that stent. Therefore, therapeutic variability results.

For example, in the case of a radioactive stent, if about 20 Grays (Gy) of radiation, as measured from 1 mm of tissue depth, are to be delivered to a vessel portion to be treated, a wide range of radiation delivery will actually occur. That is, due to the radioactive stent configuration, a non-uniform delivery, ranging from about 5 Gy to about 25 Gy is more likely delivered to the vessel portion to be treated. Due to limitations of the prior art a range of at least about 20 Gy will be delivered by a radioactive stent throughout the vessel portion to be treated in the given example. As a result, certain portions of the vessel will receive significantly more or significantly less radiation than intended. Such a variability in delivery could lead to underdose failing to reduce the risk of restenosis in certain portions of the vessel, or overdose potentially causing further vascular injury to other portions of the vessel. This variability results regardless of the therapeutic agent to be delivered.

Additionally, certain therapeutic agents are delivered to avoid a phenomenon known as "edge restenosis". Edge restenosis is prone to occur near stent ends.

Even though a stent is structurally configured to maintain the patency of a vessel lumen, edge restenosis is prone to occur with the use of radioactive stents. Edge restenosis involves the formation of vascular overgrowths in vascular areas immediately adjacent radioactive stent ends, generally within about 2 mm of each radioactive stent end. Edge restenosis is a result of delivery of a sub-threshold level of radiation to the vascular areas immediately adjacent the radioactive stent ends. These vascular areas are near or within the site of the former stenosis. They include vasculature likely to be diseased, or subjected to a recent trauma such as angioplasty. When a sub-threshold level of radiation, between about 2 Grays and about 10 Grays, as measured at 1 mm of tissue depth, reaches such vulnerable vascular areas, stenotic overgrowths may actually be stimulated. These overgrowths result in narrowed vessel portions near stent ends giving an appearance of a candy wrapper crimped around the ends of the stent. Thus, this effect is often referred to as the "candy wrapper" effect.

The occurrence of the candy wrapper effect is likely when a radioactive stent is used. This is because the intensity of radiation decreases as the source of the radiation, the radioactive stent, terminates at its ends leading to a drop of in radiation levels at vessel portions adjacent its ends. Thus, a sub-threshold radiation delivery is likely to occur near the radioactive stent ends.

As indicated, heretofore, the level of therapeutic uniformity or focus any particular stent has been able to deliver has been dependent upon that stent's configuration with respect to strut and window cell distribution. However, a stent structure (i.e. strut layout) which physically promotes maintenance of an open vessel lumen may be of a particular configuration which is not necessarily best suited for a more uniform delivery of a therapeutic agent. Additionally, this stent configuration may fail to avoid an unintended "candy wrapper" effect in which portions of the vessel adjacent the stent become narrowed.

SUMMARY OF THE INVENTION

An embodiment of the present invention provides a stent having a variable stent surface area per unit length. The variable stent surface area is used to accommodate a therapeutic agent.

Another embodiment of the present invention provides for a stent having an end and a variable stent surface area per unit length to accommodate a therapeutic agent. A decreased level of therapeutic agent in provided at the end.

An embodiment of the present invention provides for a stent having an end and a variable stent surface area per unit length to accommodate a therapeutic agent. An increased level of therapeutic agent in provided at the end.

In an embodiment of the invention a method of vessel treatment utilizing a stent with a variable stent surface area is provided. A therapeutic agent is disposed on the stent surface area to provide a patterned distribution of the therapeutic agent.

In another embodiment of the invention a method of stent manufacture is provided where indentations are cut into a surface of a stent. A therapeutic agent is disposed on the surface of the stent.

In another embodiment of the invention a method of stent manufacture is provided where struts of the stent are cut of increased thickness to provide a variable stent surface area. Therapeutic agent is disposed on the variable stent surface area.

DETAILED DESCRIPTION OF THE INVENTION

The following description makes reference to numerous specific details in order to provide a thorough understanding of the present invention. However, each and every specific detail need not be employed to practice the present invention. Additionally, well-known details, such as particular materials or methods, have not been described in order to avoid obscuring the present invention.

Figure 1:
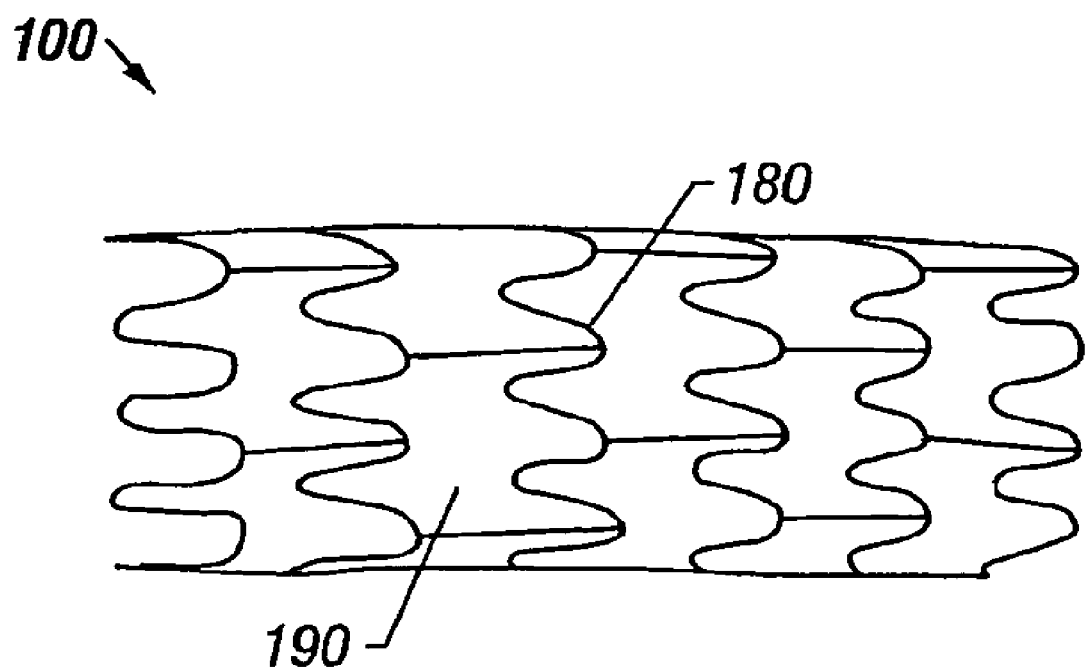
FIG. 1 is a side view of an embodiment of a stent of the present invention.

Referring to FIG. 1 an embodiment of a stent 100 of the present invention is shown. The stent 100 is formed of struts 180, which provide physical structure, and open spaces, referred to as window cells 190. The struts 180 are formed from stainless steel or other materials which are generally biocompatible. For purposes of illustration, the struts 180 shown have a cylindrical shape longitudinally. However, in alternate embodiments non-cylindrical strut 180 shapes are used. As discussed further herein the struts 180 provide a variable surface area to the stent 100.

Figure 2:
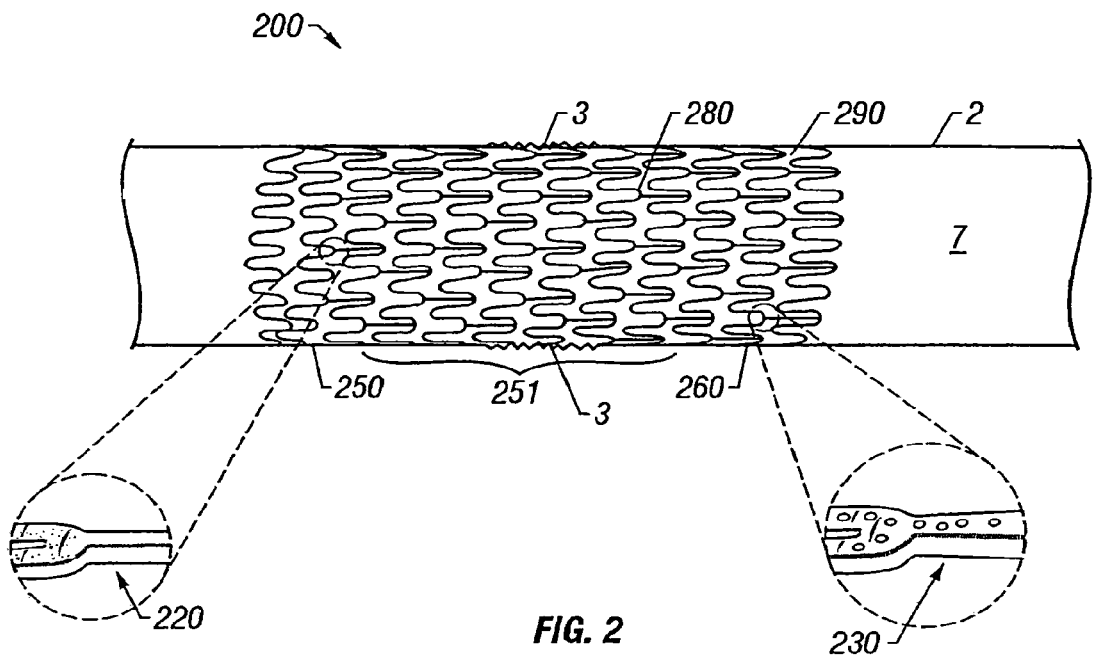
FIG. 2 is a pictorial view of an embodiment of a stent of the present invention implanted within a vessel of a patient.

Referring to FIG. 2 an embodiment of a stent 200 of the present invention is shown within a vessel 2 near the site of a former stenosis 3 to maintain the patency of the vessel lumen 7. The stent 200 of FIG. 2 is equipped with struts 280 which have variability in surface area, in terms of a change in surface area per unit length, as described further below. For each strut 280 portion, a surface area ($\gamma$) is provided which is given by the equation: $\gamma = 2\pi r l h_r$, where r is a radius (r) of the strut 280 portion, l is a length (l) of the strut 280 for the portion of the strut 280 being examined, and $h_r$ is the roughness factor ($h_r$) of the strut 280 portion.

Figure 3:
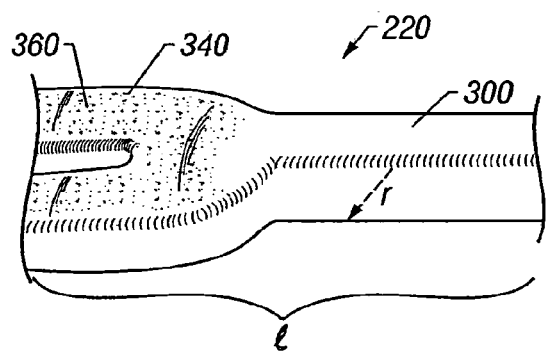
FIG. 3 is an enlarged view of an embodiment of a strut of the stent of FIG. 2.
Figure 4:
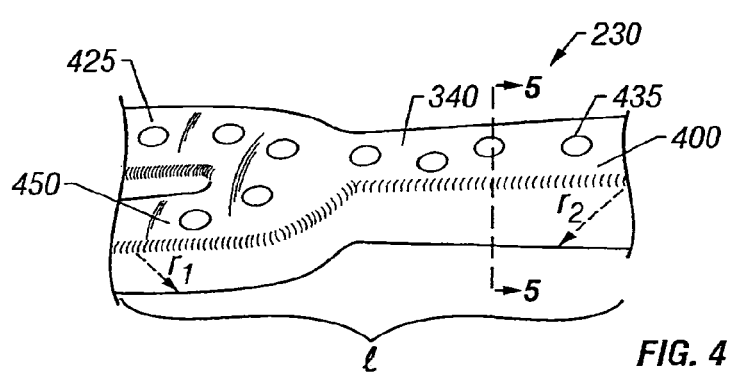
FIG. 4 is an enlarged view of an embodiment of a strut of the stent of FIG. 2.
Figure 5:
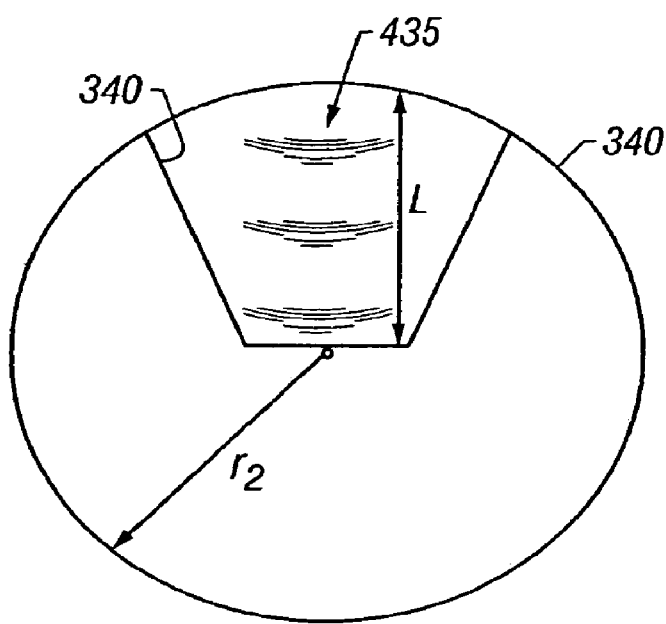
FIG. 5 is a cross sectional view of an embodiment of a strut taken along the line 5-5 of FIG. 4.

Referring to FIGS. 3 and 4, strut types 220, 230 of FIG. 2 are shown enlarged. The radius (r) (or $r_1$ and $r_2$) and a given length (l) are shown (see also FIG. 5 showing a radius ($r_2$) of a cross-section of a strut). The strut surface area ($\gamma$) includes a loading surface 340. The loading surface 340 portion of the surface area ($\gamma$) is that portion of the surface area ($\gamma$), generally facing outward (i.e. toward vessel 2 as shown in FIG. 1), that accommodates therapeutic agent. As the overall surface area ($\gamma$) increases or decreases, so does the loading surface 340. Therefore, if strut surface area ($\gamma$) varies throughout a given length (l), as it does in the embodiment shown, then the dose amount for a given length (l) (i.e. the dose concentration ($\delta$)) will vary throughout that same length (l). Given the equation: $\gamma = 2\pi r l h_r$, it can be seen that if the variables r or $h_r$ of the equation fluctuate in value, for the same given length (l), as is the case in the shown embodiment, then so too will the surface area ($\gamma$) of the strut type 220, 230 within the given length (l).

Referring to FIGS. 2 and 3, in order to vary surface area ($\gamma$) of the stent 200, certain roughened strut 220 types are provided with a surface pattern. The roughened struts 220 are those in which the variable $h_r$, referred to above, has changed in value throughout a given length (l). Or, in other words, $\gamma' = 2\pi r l \Delta h_r$. For example, where an entirely smooth surface strut is provided (not shown), the roughness factor ($h_r$) is 1.0, having no effect on the surface area ($\gamma$) of the smooth surface strut. However, if the roughness factor ($h_r$) is greater than 1.0, the surface area ($\gamma$) will correspondingly increase as shown in the present embodiment. Therefore, the dose concentration ($\delta$) of therapeutic agent deliverable to the vessel 2 is increased in corresponding portions of the strut 280 where ($h_r$) is greater than 1.0.

As shown in FIG. 3, an embodiment of a roughened strut 220 is provided of a given length (l). Moving from a first portion 360 of the given length (l) to a second portion 300, the roughness factor ($h_r$) changes as indicated by the change in roughness over that same length (l). That is, increased roughness, as indicated by the granular appearing texture of the loading surface 340, is provided near first portion 360. Alternatively, the value of the roughness factor ($h_r$) decreases and approaches a value of 1.0 near second portion 300 as shown by the smoother appearance of the loading surface 340 near second portion 300. Therefore, a roughened strut 220, as in the embodiment shown, provides one manner of varying surface area ($\gamma$) throughout a given length (l), and thus provides a variation in dose concentration ($\delta$) throughout that same length (l).

Referring to FIGS. 2 and 3, in order to increase the roughness factor ($h_r$) chemical, plasma, laser, mechanical or alternate methods of etching are used in embodiments of the invention. For example, in one embodiment the stent 200 is dry etched by sand blasting or plasma etched with argon in order to increase roughness.

Another embodiment focuses the increased roughness factor ($h_r$) at particular struts 280 by a lithography technique of coating the stent 200 with a protective polymer such as ethylene vinyl alcohol. The stent 200 is then selectively treated with a solvent, such as dimethyl sulfoxide (DMSO), dimethyl formamide (DMF), or dimethyl acetamide (DMAc), in strut 280 areas to remove portions of the protective polymer. For example, in one embodiment, a stent end 250 is dipped into the solvent to remove protective polymer from portions of the struts 280 nearer the stent end 250. By removing the protective polymer, these portions of the stent 200 are susceptible to increased roughening following application of an etching process to an exterior of the stent. Thus, once the stent 200 is etched, an increased roughness factor ($h_r$) is present at the stent end 250. However, in an alternate embodiment increasing roughness interior of the stent 1 is avoided in order to promote a flow of blood through the stent.

The roughened strut 220 embodiment shown is viewed in light of its positioning in the stent 200. It can be seen that the roughened strut 220 is found near stent end 250. The roughened strut 220 includes a loading surface 340 which has been roughened as discussed above. The degree of roughening increases moving toward the first portion 360 (nearer the stent end 250) of the roughened strut 220. Alternatively, the loading surface 340 becomes smoother moving toward a second portion 300 (nearer the stent body 251). That is, in view of the stent 200 as a whole, additional surface area ($\gamma$), and thus, increased radioactivity upon activation, is found near the stent end 250 due to the roughened strut 220 patterning provided.

Referring to FIGS. 2 and 4, in order to vary surface area ($\gamma$) of the stent 200, certain struts 280 are formed as increased thickness struts 230. The increased thickness struts 230 are those in which the radius (r), referred to above, has changed in value throughout a given length (l). Or, in other words, $\gamma''=2\pi\Delta r l h_r$.

As shown in FIG. 4, an embodiment of an increased thickness strut 230 is provided of a given length (l). Moving from a first strut portion 450 of the given length (l) to a second strut portion 400, we see that the radius ($\Delta r$) changes as indicated by the change in radius size from $r_1$ to $r_2$ respectively, with $r_2$ indicating an increased radius (i.e. $\Delta r$) from that of $r_1$. Therefore, an increased thickness strut 230 provides an alternate manner of varying surface area ($\gamma$) throughout a given length (l), and thus allowing for a variable dose concentration ($\delta$) throughout that same length (l). This pattern of surface area ($\gamma$) along the given length (l) holds true even in non-linear strut portions 425.

As shown with reference to positioning within the stent 200, the increased thickness strut 230 is shown near opposite stent end 260 of FIG. 1. As a result, increased surface area ($\gamma$) and thus, increased radioactivity upon activation, is provided near opposite stent end 260.

In a method of manufacturing the stent 200, including struts 280, the stent 200 is laser cut from, for example, a stainless steel tube. The laser cutting process is run according to an automated process to form a particular stent configuration. In order to increase or vary a radius (r) in portions of particular struts 280, the automated process is programmed to cut a strut 280 of increasing radius (r), for example, near opposite stent end 260. In this manner, an increased thickness strut 230 is provided.

Referring to FIGS. 4 and 5, a cross section taken from the line 5-5 of FIG. 4 is shown as FIG. 5. In addition to a greater amount of loading surface 340 generally, the increased thickness strut 230 of FIG. 4 includes increased size indentations 435. As shown in the embodiment of FIG. 5, the increased size indentations 435 have been cut into the loading surface 340 with a laser during manufacture to provide additional loading surface 340 at the interior of the increased size indentations 435 by providing additional interior surface with the increased size indentations 435.

Each indentation may increase surface area by about three-fold per unit area. Where the depth L is increased, surface area provided by the indentation is increased. Increased size indentations may have a depth L of about one half of the increased thickness strut 230 at the location of the indentation. Increased size indentations 435, have a depth L beyond about 60-80 microns, and are provided as thickness increases (as shown toward the opposite strut end 400 of FIG. 4). The increased size indentations 435 provide a volume as well as increased surface area ($\gamma$). In the embodiment shown, the indentations 435 are of a truncated cone shape. However, in other embodiments, other shapes are used. For example, in one embodiment of the invention, the indentations 435 are of a dimpled shape Referring to all of FIGS. 2-5, the surface area ($\gamma$) discussed in relation to the above embodiments is increased by the use of particular increased size indentations 435, an increased thickness strut 230, and a roughened strut 220. However, all of these features, alone and in any combination, are used in other embodiments to increase surface area ($\gamma$) in particular stent 200 portions and provide particularly configured and focused loading surfaces 340 for accommodating therapeutic agents. Once a particular stent 200 configuration of increased surface area ($\gamma$) is chosen and provided, it is activated with therapeutic agent, accommodated at the loading surface 340.

In an embodiment of the invention, where the therapeutic agent to be provided includes radioactive isotopes, plasma ion implantation of the isotopes into the loading surface 340 is used for activation. Embodiments of the invention employ Plasma and Ion Beam Assisted Deposition for loading. Plasma ion implantation results in radioactive ions being implanted below the loading surface 340 of the stent 200. By implanting ions below the loading surface 340, a radioactive layer is formed which is shielded from a biological environment when the stent 200 is later inserted into a patient. Plasma ion implantation involves loading the stent 200 into an isolation chamber where a plasma of radioactive ions is generated. The plasma is provided by providing a liquid or gas which includes a stable precursor to the ion type to be used. Radio Frequency (RF) or microwave power are coupled to the isolation chamber to transform the mixture into a plasma state within the chamber. Negative voltage energy pulses are then applied to the treatment stent 1 to cause implantation of ions below the loading surface 40. In various embodiments, ions such as Phosphorous ($P^{32}$), Rhenium ($Re^{188}$), Yttrium ($Y^{90}$), Palladium ($Pd^{103}$), Iodine ($I^{125}$), and Ruthenium ($Ru^{106}$) are loaded above and below the loading surface 340 in this manner.

In other embodiments, where the therapeutic agent to be provided includes bioactive drugs, alternate methods of loading onto the loading surface 340 are used. For example, a dip coating, spray, or centrifugation process is used. The dip coating process involves submerging the stent 200 in a solvent having an anti-coagulant or other drug solution. Heparin or heparin coating substances such as Duraflo®, available from Baxter International, Inc., are used as part of the drug solution.

The stent 200 is then placed into a centrifugation chamber and spun to direct the first solution to particular portions of the stent 200. The stent 200 is then dried and submerged in a second drug solution. This second drug solution also contains radioactive ions as additional therapeutic agent.

Mechanical rinsing of the stent 200 is used to remove any excess of the drug solution. Centrifugation of the stent 200 is then repeated to remove excess drug solution.

In one embodiment, where a volume is provided by increased size indentations 435, drug solution is deposited therein as a result of such methods of loading described above. In other embodiments, such methods of loading are repeated to add bioactive elutable drugs or even a separate anti-coagulant barrier to encase drug solution on the loading surface 340. The barrier is added by dipping, centrifugation and plasma deposition as indicated, or alternately by spraying or plasma polymerization.

The variability in surface area provided by any combination of the above referenced features accommodating a therapeutic agent allows delivery of therapeutic agent in a manner not limited solely to strut 280 and window cell 290 distribution. As a result, stent 200 embodiments are provided which increase therapeutic agent focus in particular areas of the stent 200.

In an embodiment of the invention, increased surface area is provided in areas of the stent 200 known to deliver an under-dose of therapeutic agent. Alternatively in another embodiment, less surface area is present in areas known to deliver an overdose of therapeutic agent. These surface area configurations are used to help avoid irregularities or significant variation in delivery of therapeutic agent.

Additionally, in an embodiment of the invention, increased surface area struts 280 are developed to focus an increased amount of therapeutic agent near stent ends 250, 260. This embodiment helps avoid delivery of sub-threshold levels of radiation to portions of a vessel immediately adjacent stent ends 250, 260 (i.e. to avoid delivery of between about 2 and about 10 Grays, as measured at 1 mm of tissue depth to the vessel 2 in this area). Likewise, another similar embodiment helps provide other therapeutic agents to help combat edge restenosis in this manner. Alternatively, variability in surface area can be used to minimize delivery of a radioactive therapeutic agent near stent ends 250, 260 in order to avoid sub-threshold radiation delivery and edge restenosis.

FIGS. 6-9 show the results of making use of particular variable surface area stent embodiments having unique focuses of therapeutic agent distribution. The results are shown with respect to dose delivery and source profiles.

Figure 6:
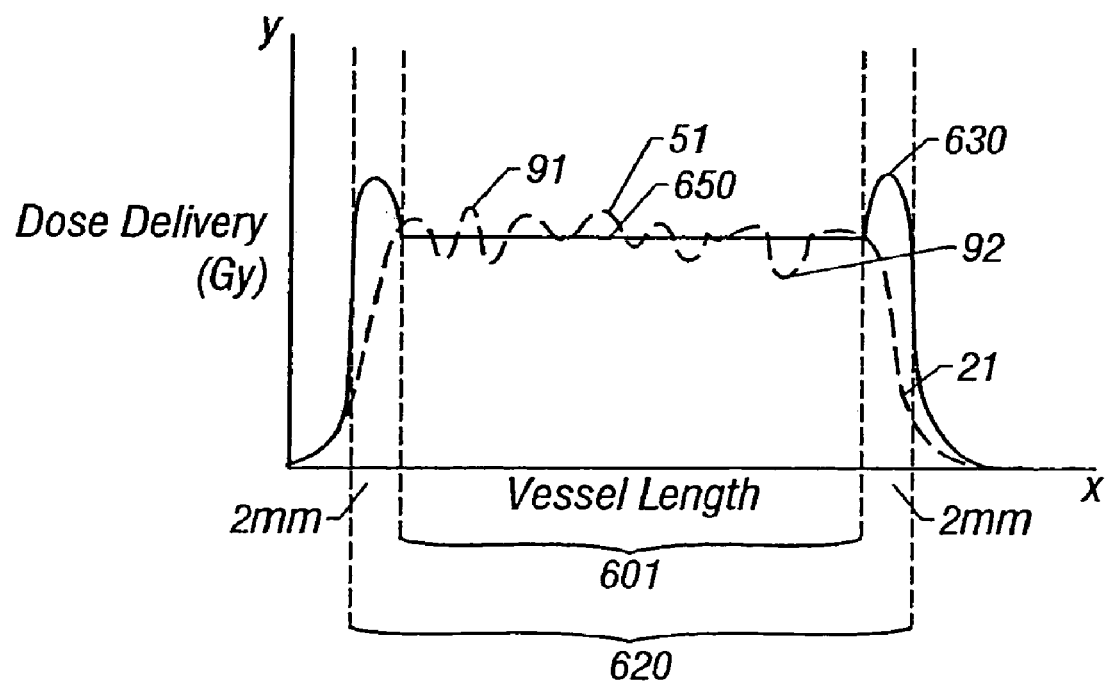
FIG. 6 is a chart depicting an embodiment of a dose delivery profile of the present invention.

For example, FIG. 6 depicts a chart indicating the distribution of therapeutic agent, in the form of radioisotopes, with respect to dose delivery for an embodiment of the invention. The x-axis, labeled "Vessel Length", includes the stent length 601 along with the treatment portion 620 of a vessel. The y-axis, labeled "Dose Delivery (Gy)", indicates the amount of radiation absorbed in Grays (Gy) throughout a vessel 2 such as that of FIG. 1 (as measured from 1 mm of vessel depth).

Figure 7:
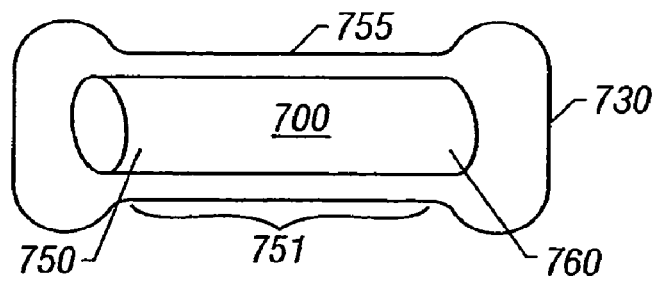
FIG. 7 is a representation of an embodiment of a source profile of the invention.

Similarly, FIG. 7 represents a source profile of a stent 700 according to the therapeutic distribution indicated in the embodiment of FIG. 6. The profile includes an extension of radioactivity 730 significantly beyond stent ends 750, 760 (i.e. hot ends) to help avoid edge restenosis. Also, a uniform field of radioactivity 755 throughout the stent body 751 is provided.

With reference to the embodiments represented in FIGS. 6 and 7, an increased amount of therapeutic agent is provided near stent ends 750, 760 due to the increased loading surface provided thereat. Therefore, where the therapeutic agent is radiation, as with the embodiments of FIGS. 6 and 7, delivery of a sub-threshold level of radiation is avoided at vessel portions immediately adjacent the stent 700 (i.e. within about 2 mm of the stent longitudinally).

Additionally, the stent 700 is configured with increased loading surface directed toward portions of the stent 700 previously responsible for a more uneven distribution of therapeutic agent. In the case of radiation delivery, a more uniform field of radioactivity 755 provides a more consistent delivery of therapeutic agent (i.e. radiation) throughout the stent body 751 of the stent 700.

A prior art distribution of radiation 51 is un-even. That is, the uniform surface area of a prior art stent may deliver a highly variable dose within a stent length 601. For example, the variable dose can include a maximum dose 91 that is 20 Gy greater than a minimum dose 92 while delivering only an average dose of 20 Gy (with all measurements taken at 1 mm of tissue depth). Alternatively, a more level delivery of radioactivity 650 is provided in embodiments of the invention. Embodiments of the invention can also include peak deliveries of radioactivity 630 to ensure avoidance of sub-threshold delivery 21 in vessel areas of concern, within about 2 mm of the stent longitudinally.

Figure 8:
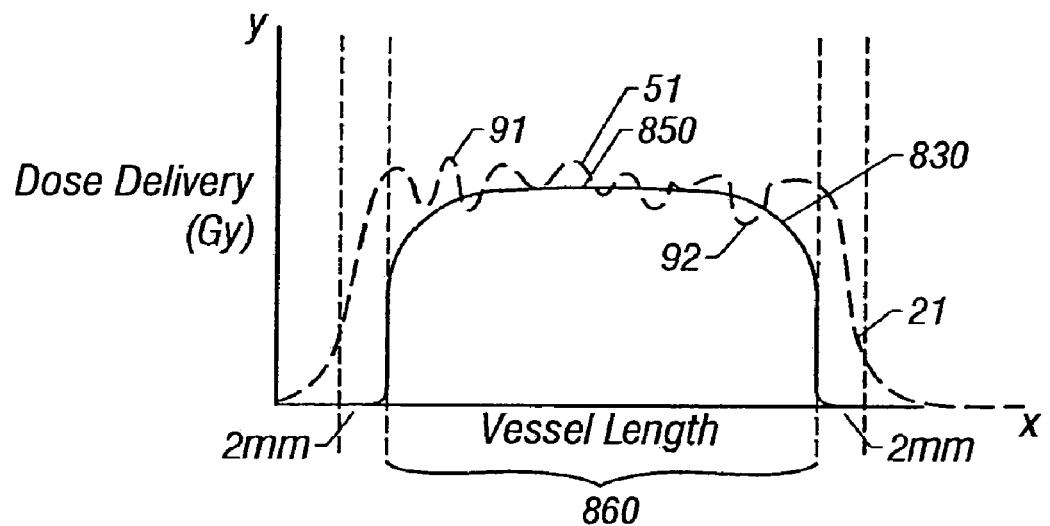
FIG. 8 is a chart depicting an embodiment of a dose delivery profile of the present invention.
Figure 9:
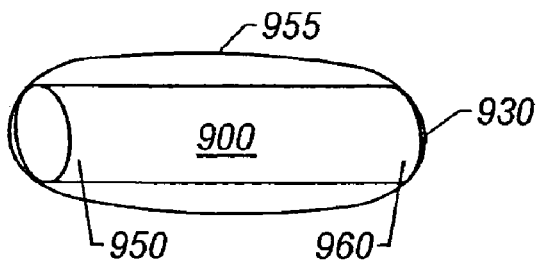
FIG. 9 is a representation of an embodiment of a source profile of the invention.

Referring to FIGS. 8 and 9, and continuing with the example of a radioactive therapeutic agent, a decreased amount of radioactivity (i.e. an early termination of radioactivity 930) is provided near stent ends in another embodiment of the invention. This is due to the decreased loading surface provided at the stent ends 950, 960 as compared to the remainder of the stent 900. Delivery of a sub-threshold level of radiation is nevertheless minimized or avoided at portions of a vessel immediately adjacent the stent 900 (i.e. within about 2 mm of the stent ends 950, 960). That is, any radiation delivered here is below a sub-threshold level to help avoid edge restenosis.

Additionally, as with FIG. 6, the stent 900 represented by FIG. 9 has been configured to have increased surface area directed toward portions of a stent 900 that would otherwise be responsible for an uneven distribution of therapeutic agent. A more uniform field of radioactivity 955 provides a more consistent delivery of therapeutic agent (i.e. radiation) throughout a stent body of the stent 900 as seen above the x-axis throughout stent length 860.

Again, by way of comparison, a prior art distribution of radiation 51 is un-even and a sub-threshold level of radiation 21 is delivered by a prior art stent to vessel areas within 2 mm of the stent. Alternatively, a more level delivery of radioactivity 850 is provided in embodiments of the invention. Embodiments of the invention can also include tapered deliveries of radioactivity 830 to ensure avoidance of sub-threshold delivery 21 in vessel areas of concern.

Embodiments of the invention described above include a therapeutic stent which is able to provide an overall pattern of therapeutic agent, where the pattern is not determined solely by strut and window cell distribution throughout the stent. Embodiments of the invention also include patterns of therapeutic agent which help avoid edge restenosis while also helping to avoid delivery of a non-uniform level of therapeutic agent throughout the portion of a vessel to be treated. While such exemplary embodiments have been shown and described in the form of particular stents having variable surface area, many changes, modifications, and substitutions may be made without departing from the spirit and scope of this invention.

What is claimed is:

1. A method of manufacturing a stent, the stent including a tubular body including a plurality of struts, the struts defining a first end segment of the body, an opposing second end segment of the body, and a middle segment of the body between the first and second end segments, the method comprising:
   performing a roughening process on the plurality of struts; and followed by
   depositing a therapeutic agent on the body so that the first or second end segment has a lesser amount or concentration of the agent than the middle segment as a result of a difference in surface roughness, the difference present between struts of the first or second end segment as compared to struts of the middle segment.

2. The method of claim 1, wherein the depositing of the agent comprises applying a composition including a polymer and the agent on the body.

3. The method of claim 1, wherein a surface area of at least some of the individual struts of the middle segment of the body is greater than a surface area of the struts of the first or second end segment so that a greater amount or concentration of the agent is carried by the struts having the greater surface area.

4. The method of claim 1, wherein the agent is an anti-coagulant.

5. The method of claim 1, wherein the agent is encased in an anti-coagulant barrier.

6. The method of claim 1, further comprising forming the plurality of struts by cutting a stent pattern from a substrate material.

7. The method of claim 1, wherein the roughening process is performed on the outside of the body while avoiding an increase in roughness inside the body.

8. The method of claim 7, wherein the roughening process includes etching by chemical method, plasma method, laser method, or mechanical method.

9. A method of manufacturing a stent, the stent including a tubular body including a plurality of struts, the struts defining a first end segment of the body, an opposing second end segment of the body, and a middle segment of the body between the first and second end segments, the method comprising:
   masking the first or second end segment with a protective layer; followed by
   etching the middle segment to increase the surface area of the middle segment; followed by
   removing the protective layer; and followed by
   depositing a therapeutic agent on the body so that the first or second end segment has a lesser amount or concentration of the agent than the middle segment as a result of the etching, the difference present between struts of the first or second end segment as compared to struts of the middle segment.

10. The method of claim 9, wherein the etching of the middle segment includes a process selected from the group consisting of dry etching, sand blasting, and plasma etching.

11. The method of claim 9, wherein after the removing of the protective layer, the agent is deposited onto the struts of the first or second end segment and onto the struts of the middle segment.

12. A method of manufacturing a stent, the stent including a tubular body including a plurality of struts, the struts defining a first end segment of the body, an opposing second end segment of the body, and a middle segment of the body between the first and second end segments, the method comprising:
   removing material from the plurality of struts to form indentations in the plurality of struts, the indentations in struts of the middle segment having a greater volume than indentations in struts of the first or second end segment; and followed by
   depositing a therapeutic agent on the body so that the first or second end segment has a lesser amount or concentration of the agent than the middle segment as a result of a difference in the volume of the indentations.

13. The method of claim 12, wherein at least some of the indentations in struts of the middle segment have a depth greater than about 60 microns.

14. The method of claim 12, wherein the agent is deposited into the indentations in the struts of the first or second end segment and into the indentations in the struts of the middle segment.

15. The method of claim 9, wherein the depositing of the agent comprises applying a composition including a polymer and the agent on the body.

16. The method of claim 12, wherein the depositing of the agent comprises applying a composition including a polymer and the agent on the body.

17. The method of claim 12, wherein the removing of the material from the body to form the indentations includes making cuts into the plurality of struts.

* * * * *